(12) United States Patent
Tankersley

(10) Patent No.: US 6,821,017 B1
(45) Date of Patent: Nov. 23, 2004

(54) RADIATED SIGNAL MEASURING DEVICE FOR RADIOGRAPHIC IMAGING EQUIPMENT

(76) Inventor: Steven C. Tankersley, 425 Pine Meadows Loop, Hot Springs, AR (US) 71901

( * ) Notice: Subject to any disclaimer, the term of this patent is extended or adjusted under 35 U.S.C. 154(b) by 101 days.

(21) Appl. No.: 09/923,149

(22) Filed: Aug. 6, 2001

(51) Int. Cl.[7] .............................................. G01D 18/00
(52) U.S. Cl. ........................................ 378/207; 378/205
(58) Field of Search ................................ 378/207, 205, 378/98.9, 4.01, 206, 197, 95, 108; 356/153, 614, 622, 623, 5.01, 5.1

(56) References Cited

U.S. PATENT DOCUMENTS

| | | | | | |
|---|---|---|---|---|---|
| 4,597,094 A | * | 6/1986 | Kleinman | ..................... | 378/95 |
| 4,896,343 A | * | 1/1990 | Saunders | ..................... | 378/95 |
| 5,239,353 A | * | 8/1993 | Ohmamyuda et al. | ......... | 356/5 |
| 5,485,502 A | * | 1/1996 | Hinton et al. | ............... | 378/117 |
| 6,120,180 A | * | 9/2000 | Graumann | .................. | 378/206 |
| 6,167,292 A | * | 12/2000 | Badano et al. | .............. | 600/407 |
| 6,282,264 B1 | * | 8/2001 | Smith et al. | ................ | 378/189 |
| 6,402,374 B1 | * | 6/2002 | Boomgaarden | ............ | 378/207 |
| 6,435,716 B1 | * | 8/2002 | Polkus et al. | ............... | 378/205 |

* cited by examiner

*Primary Examiner*—David V. Bruce
*Assistant Examiner*—Irakli Kiknadze
(74) *Attorney, Agent, or Firm*—Coats & Bennett, P.L.L.C.

(57) ABSTRACT

A measuring device determines the distance between the radiation source and the image receptor in a radiographic image machine. The measuring device directs a radiated signal from a source positioned at a first point to a detector positioned at a second point. A circuit connected to the source and the detector determines the travel time of the radiated signal. Based on the spatial relationship between the source, the detector, the radiographic imager radiation source, and the image receptor, the source to image receptor distance of the radiographic imager is determined. A display may be connected to the control circuit to output the source to image receptor distance. The radiated signal may comprise a laser beam, an ultrasonic signal, a magnetic field, or an RF electromagnetic signal.

21 Claims, 3 Drawing Sheets

RADIATED SIGNAL MEASURING DEVICE FOR RADIOGRAPHIC IMAGING EQUIPMENT

RELATED APPLICATION

The present application is based on a prior filed provisional patent application that was filed Apr. 16, 2001, and with the named inventor being Steven C. Tankersley.

FIELD OF THE INVENTION

The present invention relates generally to the field of radiographic imaging equipment and specifically to radiated signal measuring device for determining source to image receptor distance.

BACKGROUND OF THE INVENTION

The radiographic imager (colloquially known as an x-ray machine) is a well known and widely used diagnostic tool in medical facilities, research laboratories, airport security devices, and other applications. In essence, a radiographic imager comprises a radiation beam source and a radiographic image receptor. The radiation beam source produces a beam of high-energy electromagnetic waves, or x-rays, at a fixed or controllable intensity. Radiation from the radiation beam source passes through a collimator that limits or shapes the radiation beam to the desired area. The high-energy radiation beam passes through a subject, e.g., a human anatomical appendage, and subsequently strikes the radiographic image receptor, which forms an image in response to the relative intensities of the incident radiation. The image receptor may comprise a cassette containing radiographic film, a focal plane array of electro-optic elements, or other suitable receptor.

Due to the technological complexity of the radiographic imaging process, and the potential hazards associated with exposure to the radiation, radiographic imaging equipment is maintained and operated by specially trained radiologic technologists. Prior to initiating radiation exposure to obtain a radiographic image, the technologist monitors and adjusts several critical parameters of the radiographic equipment. In particular, the voltage and current applied to the radiation beam source (and hence its intensity), the duration of exposure, and the Source-to-Image receptor Distance (SID) are critical to obtaining a radiographic image of diagnostic quality.

Since the intensity of radiation incident upon the radiographic imaging receptor changes with SID according to the Inverse Square Law, even slight variations from the optimal SID may have a profound impact on radiographic density, and hence on the quality of the resulting radiographic images. Errors in the measurement of the SID can result in radiographic image being overexposed or underexposed, with resulting distortion or misrepresentation of the anatomy depicted. If the resulting image is not of diagnostic quality, a repeat examination is required, exposing the patient to additional radiation.

Modern medical radiographic imaging equipment includes various actuators and detent switches designed to precisely position the radiation beam source in relation to the image receptor, when the subject can be positioned in a predetermined location and orientation (e.g., on an integral table). However, this positioning and orientation of the subject according to predetermined parameters is not always possible. For example, patients often need x-rays in response to various injuries, which may prevent the patient from assuming a preferred position on the x-ray table. To accommodate such applications, modern medical radiographic imaging equipment includes a variety of pivoting, sliding, and gimbaled mounting apparatuses, which allow for a large degree of variation in the configuration of the radiation source and the radiographic imaging receptor. However, in any configuration other than the predetermined ones, the radiologic technologists may not be able to take advantage of the SID measurement and control capabilities of the radiographic imaging equipment. Additionally, portable units lack such integral SID controls. In such cases, the radiologic technologist must often resort to relatively crude tools, such as traditional tape measure, to ascertain and control the SID. This method is prone to error, and is imprecise even when properly performed. Consequently, the SID of the radiographic equipment may not be properly set for each exposure.

Hence, a need exists in the art for an accurate and reliable method of measuring and indicating the Source to Image Receptor Distance in radiographic equipment.

SUMMARY OF THE INVENTION

The present invention relates to a measuring device for determining the distance between two selected points associated with a radiographic imager. The measuring device includes a radiated signal source positioned at a first point and operative to project a radiated signal. The radiated signal is detected by a detector positioned at a second point. A circuit connected to the radiated signal source and the detector determines the travel time of the radiated signal. Based on the spatial relationship between the radiated signal source, the detector, the radiographic imager radiation beam source, and the radiographic image receptor, the source to image receptor distance of the radiographic imager is determined. A display may be connected to the control circuit to output the source to image receptor distance, which display may be periodically or continuously updated. The radiated signal may comprise a laser beam, an ultrasonic signal, a magnetic field, or an RF electromagnetic signal.

DETAILED DESCRIPTION OF THE INVENTION

Figure 1:
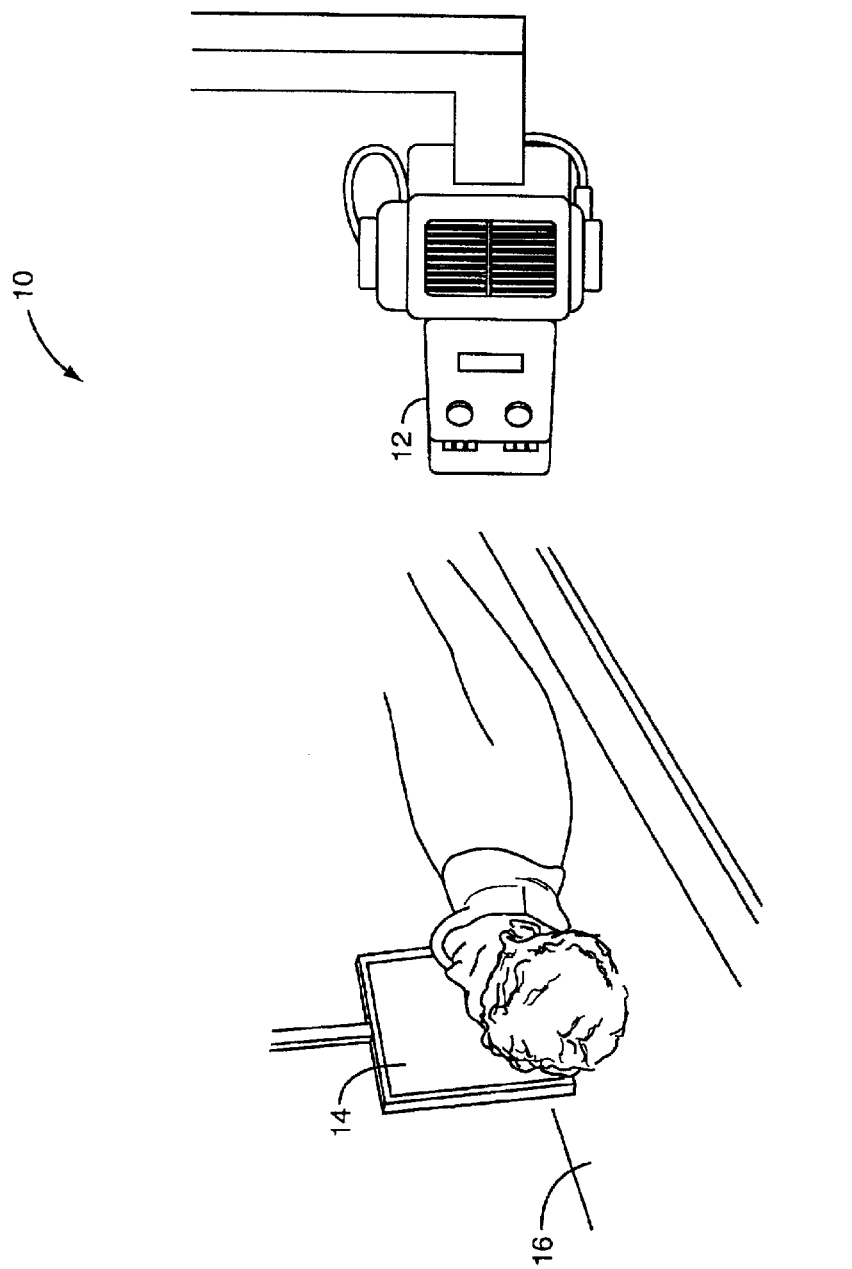
FIG. 1 is a perspective view of a representative medical diagnostic radiographic imager.

A radiographic imager utilized for medical diagnostic imaging under restrictive circumstances is depicted in FIG. 1 and indicated generally by the numeral 10. A radiation beam source and control electronics are contained in a collimator housing 12. A patient 11, due to a possible head, neck, and/or back injury, is unable to stand at a vertical chest stand, the traditional position preferred for the image depicted, a trauma lateral of the cervical spine. Consequently, the collimator housing 12 is adjusted to a lowered, horizontal position, and the patient 11 remains supine, e.g., on a stretcher. A radiographic image receptor 14, in this case, a cassette containing radiographic film, is positioned on the other side of the patient's 11 cervical spine. This specific configuration of the radiographic imager 10 is illustrative only, and represents one of any possible configurations in which the SID may need to be determined and adjusted.

To obtain radiographic images using the radiographic image equipment 10, a radiologic technologist must precisely orient the collimator housing 12 in relation to the radiographic image receptor 14, ensuring that the two are spaced apart a precise distance, which depends in general on the type of radiographic examination being conducted, the intensity of the radiation beam source, and the duration of exposure. In situations such as that depicted in FIG. 1, this Source-to-Image receptor Distance (SID) is typically measured with a tape measure or similar calibrated measuring device, or alternatively using a field size scale selector.

According to the present invention, the SID of a radiographic imager is measured by an associated distance-measuring device comprising a radiated signal source, a compatible signal detector, and an associated control circuit. The travel time of the radiated signal from the radiated signal source to the detector is measured, and the distance from the radiated signal source to the detector is determined from this travel time. The SID of the radiographic imager is then determined from the radiated signal source-to-detector distance, depending on the spatial configuration of the radiated signal source and detector in relation to the radiographic image receptor.

The distance-measuring device of the present invention may employ a broad variety of technologies to generate and detect the radiated signal. The radiated signal may, for example, comprise a laser beam, either a visible light or infrared laser. The laser beam source may comprise a gas discharge tube or a laser Light Emitting Diode (LED). The detector may comprise a photo-diode responsive to the relative frequency of the laser beam, a charge-coupled imaging device, or the like. Alternatively, the radiated signal may comprise an ultrasonic acoustic signal, with a suitable ultrasonic source and detector, as are well known in the art. As another example, the radiated signal may comprise a Radio Frequency electromagnetic wave, such as an X or K band radar signal, with the associated source and detector comprising appropriately configured and tuned oscillators, transmitters, receptors, and antennas, as are well known in the art. Particularly for the measurement of small distances, the radiated signal may comprise a magnetic flux, for example generated by an electromagnet and detected by a Hall effect sensor. In general, a wide array of radiated signal measuring devices are known in the art, and may be advantageously adapted to the SID measuring device of the present invention.

Figure 2:
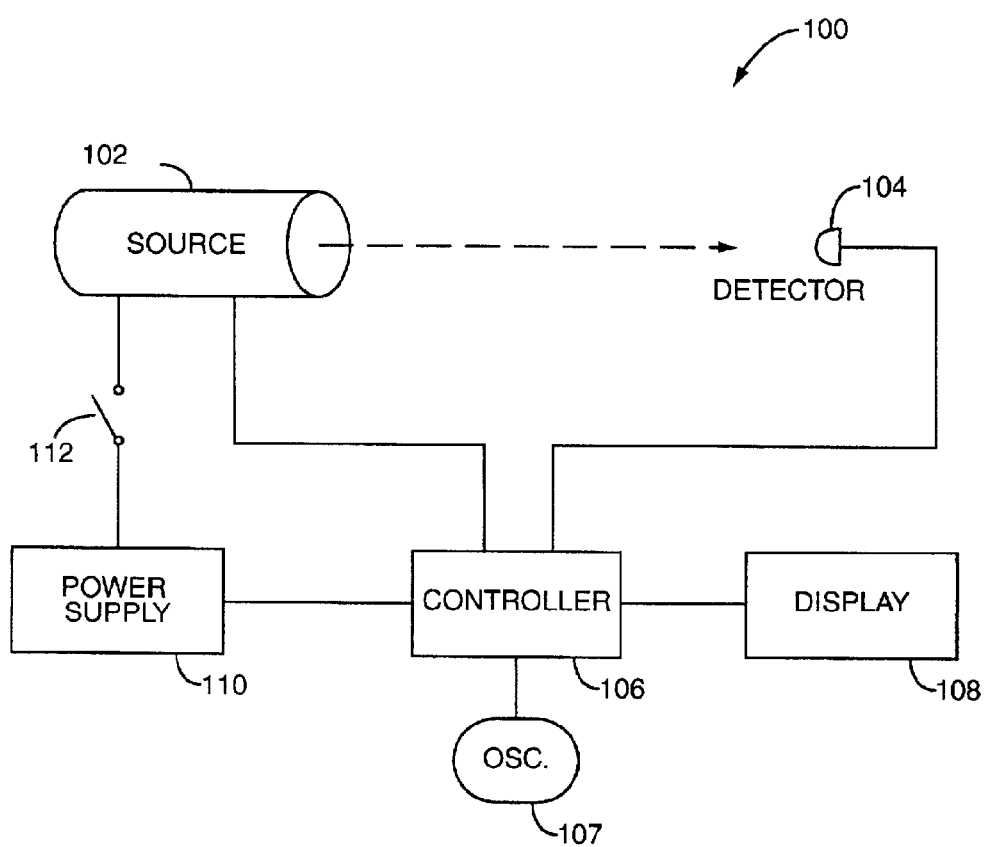
FIG. 2 is a block diagram of a radiated signal SID measurement device, according to one embodiment of the present invention.

In one exemplary embodiment, the SID measuring device of the present invention comprises a laser rangefinder, a block diagram of which is depicted in FIG. 2 and indicated generally by the numeral 100. The measuring device 100 comprises a laser source 102, a laser light detector 104, a controller 106, and a display 108. The laser source 102 and controller 106 are powered by a power supply 110, selectively coupled to the source 102 via switch 112. The laser source 102 may comprise a laser gas discharge tube, such as for example, a helium-neon (He-Ne) laser tube, with suitable high power electronics and control circuitry. Alternatively, the laser source 102 may comprise any of a broad array of available laser LEDs and suitable associated drive electronics. The laser source 102 may emit laser light within the human visible spectrum, or alternatively may emit an infrared laser beam. Laser light detector 104 may comprise a photo-diode responsive to the frequency of the laser beam emitted by the laser source 102. The detector 104 may additionally include appropriate associated thresholding and drive electronics.

Both the laser source 102 and the laser light detector 104 are connected to, and operate under the control of, controller 106. Control circuit 106 may in general be implemented in a broad variety of ways. In one embodiment, controller 106 includes a digital microprocessor, microcontroller, or digital signal processor, the operation of which may be specified by a software program. The controller 106 receives a high-frequency periodic oscillating signal, or "clock" signal, from an oscillator 107. Based on the known frequency of the oscillator 107, the controller 106 is operative to measure the elapsed time from the initiation of a laser beam projected from the source 102 until the detection of that beam incident upon the laser detector 104. The power supply 110 provides appropriate electrical power to both the laser source 102 and the controller 106. In one embodiment, the power supply 110 is coupled to the source 102 via a switch 112, operated by the radiologic technologist. This allows the laser source 102 to be energized only when the technologist is positioning the collimator housing 12 relative to the radiographic image receptor 14 in preparation for a radiographic exposure. This selective control reduces any potential vision hazard associated with the laser source 102, and in the case of a visible laser beam, may alleviate potential apprehension on the part of the diagnostic patient.

In one embodiment, a display 108 is connected to and controlled by the controller 106, and is operative to display the radiographic imager SID to the radiologic technologist. The display is preferably continuously updated to reflect instantaneous changes in the SID as the technologist positions the collimator housing 12. The SID may be displayed in any appropriate units, under the control of controller 106. The display 108 may comprise a Liquid Crystal Display (LCD) of a suitable size and configuration, a series of seven-segment LED display characters, or other electronic numerical display as are well known in the art. Alternatively, in radiographic imaging equipment containing a separate display or interface, e.g., whereby the radiologic technologist may monitor and control parameters of the radiation source such as voltage and current, the display 108 may comprise an interface circuit compatible with said existing display, such that the SID display is integrated with the other radiographic equipment information.

The radiated signal source 102 and the detector 104 of the radiated signal SID measuring device of the present invention may be arranged in a variety of ways to effect measurement of the SID. The radiated signal source 102 may be affixed to the exterior of the collimator housing 12 of the radiographic imager 10 (see FIG. 1) via a moveable bracket, allowing the radiated signal to be independently directed, or "aimed," to any specific desired point. In this configuration, the distance from the radiated signal source 102 to the radiation beam source within the collimator housing is fixed and known, and can be easily accounted for in the SID calculations. Alternatively, the radiated signal source 102 may be mounted in the interior of the collimator housing 12, either coincident with or a known distance from the radiation beam source. Two basic configurations of the radiated signal source 102 and detector 104 are contemplated (each dictating a difference placement of the detector 104): a direct distance measurement and a reflected measurement.

In a direct distance measurement, the radiated signal source 102 is fixed in a known spatial relationship with the radiation beam source, such as for example, affixed to the collimator housing 12. The detector 104 is positioned on or adjacent the radiographic image receptor 14, such as for example, embedded in or clipped onto a radiographic film cassette. The radiated signal source 102 and detector 104 are aligned such that the radiated signal (e.g., the laser beam) travels in a straight line from the radiated signal source 102 to the detector 104. In this configuration, calculation of the SID is simply the measured travel time of the radiated signal from the radiated signal source 102 to the detector 104, multiplied by the known propagation speed of the radiated signal (e.g., $3 \times 10^8$ m/sec for a laser beam). Mathematically, $$SID = t_{travel} * S_{prop} \text{ where}$$

SID=Source to Image receptor Distance;
$t_{travel}$=travel time of the radiated signal from the radiated signal source to the detector; and
$S_{prop}$=propagation speed of the radiated signal.

Figure 3:
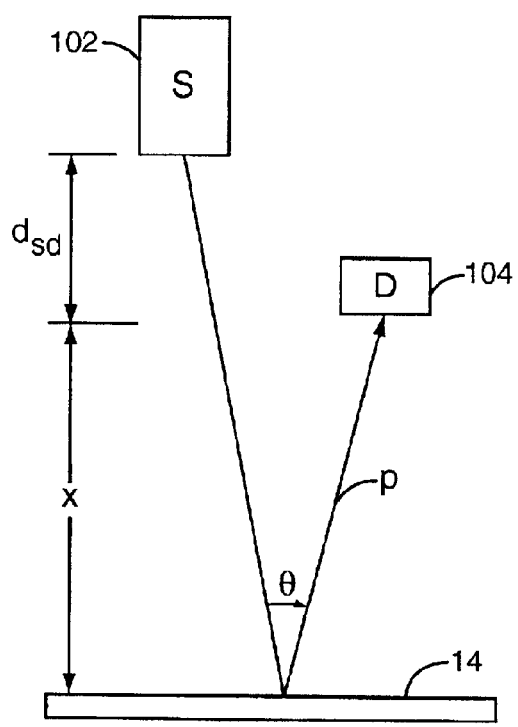
FIG. 3 is a schematic representation of the reflected signal path of the radiated signal of the present invention, according to one embodiment thereof.

In a reflected configuration, both the radiated signal source 102 and the detector 104 are affixed in a known spatial relationship to the radiation beam source, such as for example, affixed to the collimator housing 12. The radiated signal is in this case directed from the radiated signal source 102 to a surface substantially in the plane of the radiographic image receptor, for example, a radiographic film cassette, in a region that is not occupied by the anatomy of the diagnostic subject. In situations where the diagnostic subject covers substantially all of the radiographic image receptor, the radiated signal may be reflected off of an adjacent surface, substantially coplanar with the radiographic image receptor, such as for example, a stretcher or back board. In this configuration, the radiated signal is directed from the radiated signal source 102 to the plane of the diagnostic image receptor 14, and is reflected to the detector 104. In general, the radiated signal source 102 and detector 104 need not be coplanar with respect to the radiographic image receptor 14. This arrangement is depicted in FIG. 3.

In this configuration the SID is calculated by first determining the path length of the radiated signal, indicated as p. As in the case of direct illumination, the distance p is given by multiplying the travel time of the radiated signal from the radiated signal source 102 to the image receptor 14 and thence to the detector 104, multiplied by the propagation speed of the radiated signal. The known offset of the radiated signal source 102 and detector 104, if any, indicated by the quantity $d_{sd}$ in FIG. 3, is subtracted from the signal path length p (regardless of whether the radiated signal source 102 or detector 104 is positioned closest to the image receptor 14). The remaining distance x is then half of the remaining path length. Finally, the SID is the radiated signal source-to-detector offset (if any) plus the quantity x. Note that this calculation assumes that the angle θ formed between the incident and reflected radiated signal path is small. In this case, sin θ is negligible, and does not affect the calculation of p as described. For a wider angle θ, one of skill in the art may easily derive distance calculation equations to account for the angle. Mathematically, $$p = t_{travel} * S_{prop}$$

$$x = \frac{p - d_{sd}}{2} \text{ and}$$

$$SID = x + d_{sd} \text{ where}$$

p=radiated signal path length from radiated signal source to detector;
$t_{travel}$=travel time of the radiated signal from the radiated signal source to the detector;

$S_{prop}$=propagation speed of the radiated signal;
$d_{sd}$=distance of offset between radiated signal source and detector in direction of image receptor;
x=distance between the image receptor plane and the closer of the radiated signal source and detector; and
SID=radiation beam source to mage receptor distance;

By use of the radiated signal measuring device of the present invention, the SID of a radiographic imager may be easily and accurately set prior to each exposure, particularly in situations where the SID setting facilities of the radiographic imaging equipment may not be fully utilized. This increases the quality of the resulting diagnostic image by ensuring the proper relationship between the radiation beam energy (e.g., as controlled by the radiologic technologist by varying the voltage and current applied to the radiation beam source), the image receptor type, the SID, and the characteristics of the imaging subject.

Although the present invention has been described herein with reference to a diagnostic medical radiographic imager, one of skill in the art will readily recognize that the invention is not so limited; it may be advantageously applied to improve the accuracy and quality of any radiographic imaging equipment. For example, and without limitation, the SID measuring device may be used in portable and field-deployed radiographic imagers utilized by emergency medical personnel and the military, in particular in situations where radiographic imaging must be performed on a stretcher, hospital bed or immobilization device such as a backboard used to transport trauma victims. In these situations, a separate physical measuring device may be misplaced or broken, and even if maintained in operable condition, represents an additional piece of equipment that must be stored, transported and inventoried. The present invention may also be advantageously utilized in surgical situations, where a patient's location and orientation may be restricted, and where the introduction of physical measuring devices such as scales and standards may contaminate the sterile field.

Furthermore, the present invention finds utility in research and laboratory applications, where the subject matter may require varied configurations of the radiographic image equipment, and where SID accuracies more precise than those obtainable with conventional measuring devices are required. As yet another example, the present invention may be useful in various security and law enforcement applications, such as airport terminals, border crossings, diplomatic installations, and the like. Such applications encompass both fixed radiographic imagers, such as luggage inspection, and portable units, such as those used by bomb squads and contraband inspectors. In both fixed and portable radiographic imaging equipment, quick, accurate positioning of the radiation beam source and image receptor, without the use of external devices, is advantageous.

Although the present invention has been described herein with respect to particular features, aspects and embodiments thereof, it will be apparent that numerous variations, modifications, and other embodiments are possible within the broad scope of the present invention, and accordingly, all variations, modifications and embodiments are to be regarded as being within the spirit and scope of the invention. The present embodiments are therefore to be construed in all aspects as illustrative and not restrictive and all changes coming within the meaning and equivalency range of the appended claims are intended to be embraced therein.

What is claimed is:

1. A radiographic imager having a measuring device for determining the distance between an x-ray source and an image receptor associated with the radiographic imager, comprising:

a radiated signal source positioned at one of the x-ray source or image receptor associated with said radiographic imager and operative to project a radiated signal;

a detector positioned at the other one of the x-ray source or image receptor associated with said radiographic imager and operative to detect said radiated signal; and a circuit connected to said radiated signal source and said detector, said circuit operative to determine the travel time of said radiated signal between said x-ray source and said image receptor, and thereby determine the distance between the x-ray source and the image receptor.

2. The device of claim 1, wherein said radiated signal is projected from said radiated signal source to said detector in a straight line, and said distance between said x-ray source and image receptor is determined by multiplying the propagation speed of said radiated signal by said travel time of said radiated signal.

3. The device of claim 1, further comprising a surface associated with said radiographic imager, and wherein said radiated signal is directed from said signal source to said surface;

said radiated signal is reflected from said surface to said detector; and the distance between said surface and the closer of said signal source and said detector is calculated as:
  the propagation speed of said radiated signal multiplied by said travel time of said radiated signal
  less the distance from said source to said detector in the direction of said surface.

4. The device of claim 1, wherein said radiated signal is selected from the group including a laser beam, ultrasonic signal, magnetic field, and RF electromagnetic signal.

5. The device of claim 1, additionally comprising a display connected to said circuit, said display operative to display said distance between said two selected points.

6. The device of claim 5, wherein said display is continuously updated as said distance between said two selected points changes.

7. The device of claim 1, additionally comprising a power source connected to said radiated signal source via a switch, whereby said radiated signal source is placed in an operative state or an inoperative state responsive to said switch configuration.

8. A method of determining the distance between an x-ray source and an image receptor associated with a radiographic imager, comprising:

projecting a radiated signal from one of the x-ray source or the image receptor associated with said radiographic imager;

detecting the projected signal at the other of the x-ray source or image receptor associated with said radiographic imager; and determining the distance between said x-ray source and image receptor based on the travel time of said radiated signal.

9. The method of claim 8, further comprising continuously displaying said distance to a radiologic technologist as said distance is changed by altering the relative position of a of an x-ray source and the image receptor.

10. A radiographic imager, comprising:

a collimator housing containing a radiation beam source;

an image receptor for receiving radiation and responsively forming a diagnostic image; and a measuring device operative to directly determine the distance between said collimator housing and said image receptor by calculating the travel time of a radiated signal directed from a radiated signal source to a detector, said radiated signal source affixed to said collimator housing and said detector positioned in a known spatial relationship with said source and said image receptor.

11. The radiographic imager of claim 10, further comprising a switch for toggling said radiated signal source between an operative and an inoperative condition.

12. The radiographic imager of claim 10 wherein said measuring device comprises a radiated signal source for emitting a radiated signal and a detector spaced from said radiated signal source and operative to detect the radiated signal emitted by the radiated signal source.

13. The radiographic imager of claim 12 including a circuit operatively associated with said radiated signal source and said detector for the determining the distance between said radiation beam source and said image receptor.

14. The radiographic imager of claim 13 wherein said circuit is operative to determine the travel time of a radiated signal passing from the radiated signal source to the detector.

15. The radiographic imager of claim 10 wherein said radiated signal source is selected from the group including a laser beam source, an ultrasonic signal source, a magnetic field source, and an RF electromagnetic signal source.

16. The radiographic imager of claim 10 including a display that is operative to display the distance between said radiation beam source and said imager receptor.

17. The radiographic imager of claim 10 wherein said detector is positioned in the plane of said image receptor and wherein said radiated signal travels from said radiated signal source directly to said detector.

18. The radiographic imager of claim 10 wherein said detector is positioned proximate said radiated signal source and wherein said radiated signal travels from said radiated signal source to said image receptor and is reflected back to said detector.

19. A radiographic imager, comprising:

an image receptor;

an x-ray source spaced from said image receptor; and a radiated signal source for directly determining the distance between said image receptor and said x-ray source, said radiated signal source selected from the group including a laser beam source, an ultrasonic signal source, a magnetic field source, and an RF electromagnetic signal source.

20. The radiographic imager of claim 19 wherein said radiated signal source is operative to direct a radiated signal to a detector associated with said radiographic imager and wherein the distance between said x-ray source and said image receptor is a function of the travel time of the radiated signal to move between the radiated signal source and the detector.

21. The radiographic imager of claim 19 further including a controller operatively associated with the radiated signal source and the detector for the determining the distance between the x-ray source and the image receptor based on the travel time of the radiated signal in moving from the radiated signal source to the detector.

* * * * *